United States Patent [19]

Nappholz et al.

[11] 4,393,874
[45] Jul. 19, 1983

[54] BRADYCARDIA EVENT COUNTING AND REPORTING PACER

[75] Inventors: Tibor A. Nappholz, Drummoyne, Australia; Barry Hinch, Princes Risborough; David B. Shaw, Exeter, both of England

[73] Assignee: Telectronics Pty. Ltd., Lane Cove, Australia

[21] Appl. No.: 372,026

[22] Filed: Apr. 26, 1982

[51] Int. Cl.³ .............................................. A61N 1/36
[52] U.S. Cl. ........................... 128/419 PT; 128/697; 128/703
[58] Field of Search .......... 128/697, 419 PG, 419 PT, 128/702, 703, 706

[56] References Cited

U.S. PATENT DOCUMENTS

| | | | |
|---|---|---|---|
| 3,144,019 | 8/1964 | Haber | 128/419 PG |
| 3,460,542 | 8/1969 | Gemmer | 128/419 PG |
| 3,524,442 | 8/1970 | Horth | 128/703 |
| 3,557,796 | 1/1971 | Keller, Jr. et al. | 128/419 PG |
| 3,633,569 | 1/1972 | Brayshaw et al. | 128/702 |
| 3,742,938 | 7/1973 | Stern | 128/419 PT |
| 3,921,642 | 11/1975 | Preston et al. | 128/419 PG |
| 4,137,908 | 2/1979 | Degonde et al. | 128/697 |
| 4,163,451 | 8/1979 | Lesnick et al. | 128/419 PG |
| 4,307,725 | 12/1981 | Sowton et al. | 128/419 PG |

Primary Examiner—William E. Kamm
Attorney, Agent, or Firm—Gottlieb, Rackman and Reisman

[57] ABSTRACT

There is disclosed an event counting and reporting heart pacer which is useful for patients who suffer from bradycardia. The pacer operates in a demand mode with a 2.5-second escape interval. A count is maintained of the number of pauses each of which exceeds this escape interval. Four successive pauses, each of which exceeds 2.0 seconds but is less than 2.5 seconds, are treated as a single 2.5-second pause. Following the detection of each pause, the escape interval is reduced to 1.2 seconds and the counter is inhibited from further operation; the counter is enabled and the 2.5-second escape interval applies once again only after a spontaneous heartbeat is detected within 1.2 seconds of the preceding beat. When a maximum count of 128 pauses is reached, the system thereafter operates with fixed 1.2-second escape interval. Upon application of an external magnet, the pacer generates a continuous series of pulses at a high rate whose number is proportional to the current count; a physician, by observing an EKG trace, can thus determine the number of pauses which were counted. Interrogation of the pacer in this way also resets the counter so that another counting cycle can begin.

27 Claims, 2 Drawing Figures

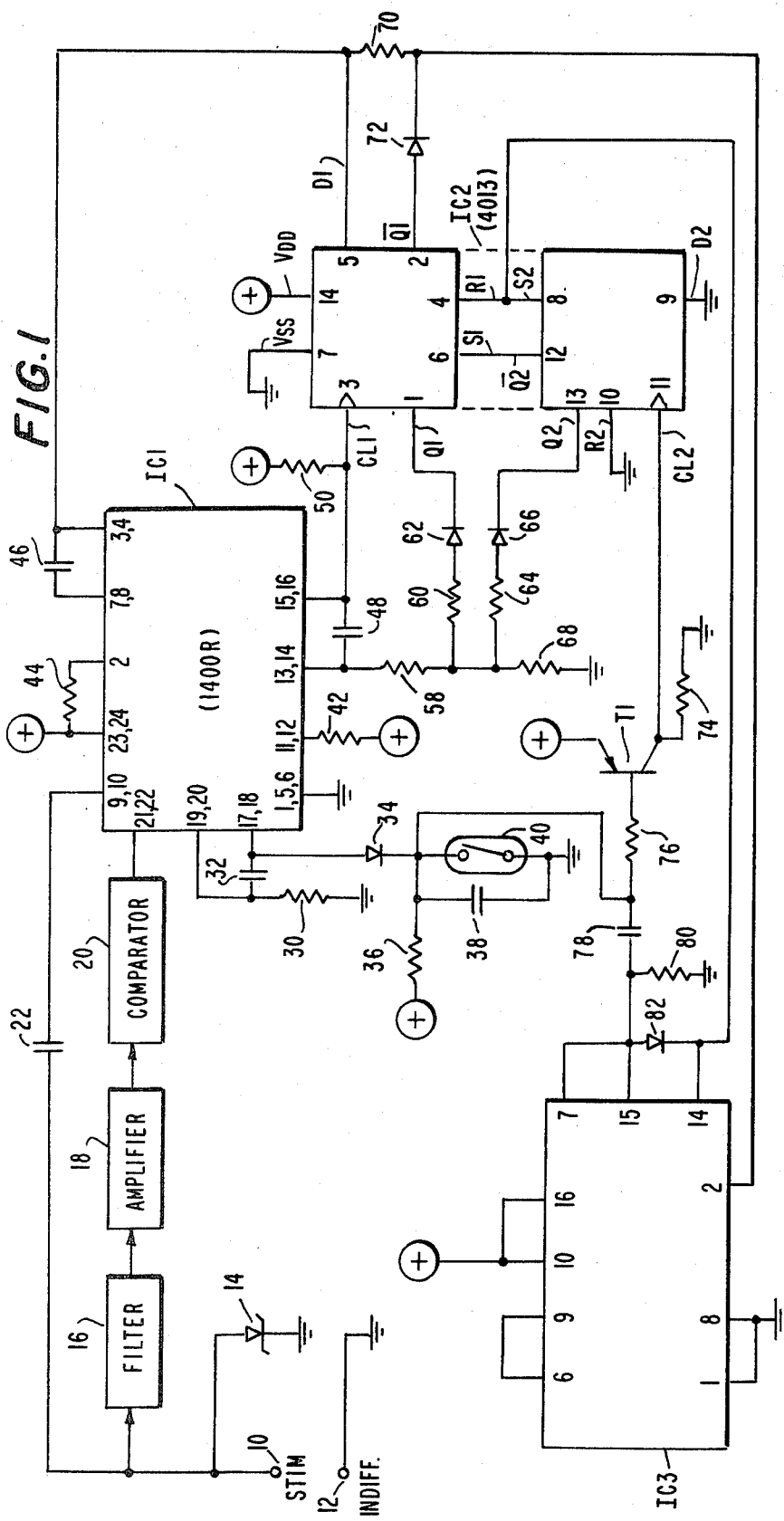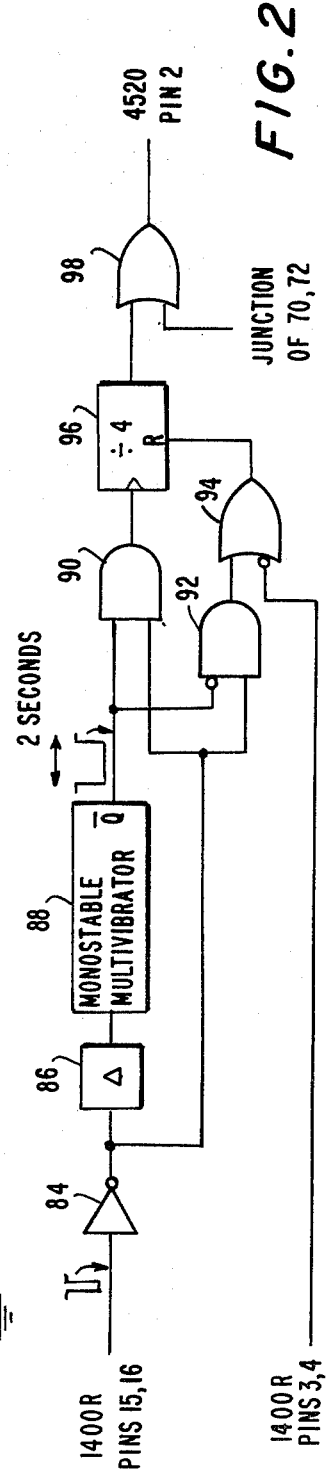

BRADYCARDIA EVENT COUNTING AND REPORTING PACER

DESCRIPTION

This invention relates to heart pacers, and more particularly to heart pacers which are capable of counting bradycardia events of interest and reporting on them.

In recent years, heart pacers have become quite sophisticated and new types of pacers, for controlling new functions, are being introduced continuously. However, while pacing functions have been expanded, the diagnostic capabilities of present-day pacers have not advanced as significantly. A conventional pacer can usually "report" on its battery or some other electronic condition, e.g., by generating a continuous sequence of pacing pulses whose rate is dependent upon the value of the parameter of interest. Conventional pacers, however, do not provide cardiac diagnostic information.

There have been proposals in the prior art for providing a pacer with a minimal diagnostic and reporting capability. For example, there are pacers which detect a bradycardia condition, an excessive pause between two spontaneous beats, and which allow for interrogation. Such a unit can simply inform the physician whether at least one pause has occurred; it is incapable of advising the physician about how many such pauses have taken place.

In one prior art pacer, however, pauses which exceed a preset interval are actually counted. Upon application of a magnet, the pacer generates a number of pulses dependent upon the number of pauses which were counted subsequent to the last interrogation. This pacer is described in an article entitled "A Diagnostic Function For A Pacemaker", by Attuel et al, which appeared in the Proceedings of the Sixth World Symposium on Cardiac Pacing, held in Montreal on Oct. 2-5, 1979. The short-coming of this prior art pacer is that it counts and reports only pauses which exceed a single threshold interval. In diagnosing a bradycardia condition, this may provide insufficient information.

It is a general object of our invention to provide a pacer which is capable of counting and reporting on a number of different bradycardia events of interest which have taken place.

In accordance with the principles of our invention and in the illustrative embodiment thereof, the pacer operates initially with an "escape interval" of 2.5 seconds. If a spontaneous heartbeat does not occur within 2.5 seconds of the preceding beat, the pacer generates a stimulating pulse. The internal timing mechanism is reset not only when a pacing pulse is generated, but also when a spontaneous beat is detected. If a spontaneous beat is detected within 2.5 seconds of the preceding beat, a pacing pulse is not generated and instead the timing mechanism is re-triggered.

Whenever a pause of 2.5 seconds occurs, a pacing pulse is generated and the count maintained in a counter is incremented. The escape interval is reduced to 1.2 seconds, an effect known as "hysteresis", and normal demand pacing ensues until a spontaneous beat is detected. As soon as such a beat is detected, the escape interval is increased to 2.5 seconds once again so that the pacer can "look" for another pause. The maximum allowable count is 128. Should 128 pauses be counted, the system mode of operation is changed. No further pauses are counted, and instead the escape interval is permanently shortened to 1.2 seconds.

Whenever the physician desires to know how many pauses have been counted, he applies a magnet to the chest of the patient. The pacer thereupon generates a number of pulses at a relatively fast, but not dangerous, rate of 80 pulses per minute. The number of pulses generated is equal to 128 minus the initial count in the counter upon interrogation. By counting the number of rapid pacing pulses which appear on an EKG trace, the physician can determine the number of pauses which occurred subsequent to the last interrogation simply by subtracting the number of rapid pulses on the trace from 128. Following interrogation, the counter is reset so that another counting and reporting cycle can commence. (Although not shown in the illustrative embodiment of the invention, it is to be understood that the pacer may be programmable as is known in the art. Once the physician determines the information of interest, he can re-program the pacer to operate as a normal demand device—with a permanent escape interval, for example, of 1.2 seconds without having to count up to 128 pauses.)

The present invention relates primarily to what is considered to be a pause. Thus far, a pause has been described as the absence of a heartbeat for 2.5 seconds. Some physicians, however, consider a number of pauses in succession, each shorter than a "long" pause but also longer than a normal escape interval, to be a single "pause" indicative of a bradycardia condition. For this reason, we provide a circuit which, in the illustrative embodiment of the invention, counts four successive pauses, the duration of each of which is greater than 2 seconds but less than 2.5 seconds. Whenever four such pauses are counted in succession, the counter is incremented. Thus the total count is the sum of the number of 2.5-second pauses and the number of shorter pause sequences (of four successive pulses each) which have taken place subsequent to the last interrogation. It will be apparent that should the two kinds of events need to be distinguished, a pacer could be provided which includes two counters, together with a mechanism for allowing the counters to report one after the other.

Further objects, features and advantages of our invention will become apparent upon consideration of the following detailed description in conjunction with the drawing, in which:

FIG. 1 depicts a basic event counting and reporting pacer in which our invention may be incorporated; and FIG. 2 depicts the illustrative embodiment of our invention, in the form of an add-on circuit which treats four successive short pauses as a single longer pause which is counted as a single event.

Chip IC1 is a conventional timing oscillator/pulse doubler (1400R) used in the manufacture of heart pacers by Telectronics Pty. Ltd. in its standard line of heart pacers, the chip being available from Amalgamated Wireless Microelectronics Pty. Ltd. of Sydney, Australia. Indifferent electrode 12 is grounded, and stimulating electrode 10 is connected through a standard protective Zener diode 14 to ground. Stimulating pulses generated by chip IC1 at pins 9, 10 are extended through capacitor 22 to the stimulating electrode. (Many of the connections to the chip are made to two pins, which are connected together on the chip for the sake of reliability, as is known in the art.) The stimulating electrode is also connected to the input of filter 16, the output of the filter being amplified by amplifier 18 and compared to a threshold level by comparator 20. A positive pulse at pins 21, 22 of chip IC1 represents a detected heartbeat. Although elements 16, 18 and 20 are shown as separate units, it will be apparent to those skilled in the art that in a conventional pacer the functions of these elements may be performed by a single chip with some connected discrete components.

Chip IC1 is the "heart" of the pacer, and its input and output signals which are necessary for an understanding of the subject invention will now be described. A positive pulse appearing at pins 21, 22 is internally coupled through the chip to pins 19, 20. The pulse is coupled through capacitor 32 to pins 17, 18. A trigger input at pins 17, 18 resets the internal oscillator in chip IC1 and starts a new timing cycle. Diode 34 is normally reverse biased by the battery potential applied through resistor 36. Should reed switch 40 be closed, however, pins 17, 18 are shorted through the diode and the switch to ground, and chip IC1 no longer responds to detected heartbeats; instead, it operates in a free-running mode.

Chip IC1 operate in either the synchronous or the inhibit mode. In the former a stimulating pulse is generated at pins 9, 10 whenever a heartbeat is detected in order to reinforce it, and in the latter such a reinforcement pulse is not generated. Because pin 1 is grounded (along with pins 5 and 6), chip IC1 operates in the inhibit mode.

Coincident with each pacing pulse at pins 9, 10, a negative pulse is generated at pins 3, 4. A negative pulse also appears at pins 15, 16 whenever a pulse appears at pins 3, 4 to indicate that a stimulus has been generated. However, a negative pulse also appears at pins 15, 16 whenever a heartbeat is detected, in which case a pulse does not appear at pins 3, 4 or pins 9, 10 since the chip is operated in the inhibit mode.

Capacitor 46 is a charge storage capacitor which discharges through pins 9, 10 whenever a stimulating pulse is required. The actual magnitude of the pulse is twice that of the battery, as is known in the art, since between pulses each of capacitors 22 and 46 charges to the full battery supply; whenever a pulse is to be generated, the two capacitors are connected in series and discharge through the electrodes. Capacitor 48, connected between pin pairs 13, 14 and 15, 16, is the rate timing capacitor. This capacitor, together with the total resistance connected at its left side, determines the escape interval of chip IC1. If both of diodes 61 and 62 are reverse biased, then the connected resistance is simply the series impedance of resistors 58 and 68. The total impedance decreases, however, depending upon which of diodes 62 and 66 has its cathode connected to a ground potential so that the respective resistor 60 or 64 is in parallel with resistor 68. Resistor 42 determines the width of each pulse which is generated.

Chip IC2 is a 4013 dual D-type flip-flop. The device is shown as two separate flip-flops, with the dashed lines indicating that the two devices are contained in the same chip. If the S1 input of the upper flip-flop is high in potential when the R1 input is low, then the Q1 output is high and the $\overline{Q}$ output is low. Opposite output conditions are obtained when the reset input R1 is high in potential and the S1 input is low. Similar remarks apply to the lower flip-flop. A positive transition at either clock input CL1 or CL2 causes the respective flip-flop to assume the state represented at its respective data input D1 or D2. For example, if the D1 input is low in potential when the CL1 input goes high, the Q1 output goes low and the $\overline{Q1}$ output goes high. Since the $\overline{Q2}$ output of the lower flip-flop is connected to the S1 input of the upper flip-flop, the state of the latter affects the state of the former. The reset input of the upper flip-flop and the set input of the lower flip-flop are both connected to pin 14 of chip IC3; a positive potential at this pin holds the upper flip-flop reset and the lower flip-flop set, as will be described below.

Chip IC3 is a 4520 dual synchronous up counter. The chip includes two four-bit counters. The most significant bit output of one counter at pin 6 is connected to the clock input of the other counter at pin 9. The second counter is permanently enabled by the positive potential applied to pin 10, and the first counter is enabled whenever a negative step is applied to pin 2. Because the clock pin 1 of the first counter is tied to ground potential, a negative step applied to pin 2 increments the first counter. The net result is that the two counters act as a single 8-bit counter. Pins 7 and 15 are the reset inputs for the two counters, and thus a positive potential at these two pins resets the overall counter. Pin 14 is the most significant bit output of the second counter. When the overall counter cycles from a count of 127 to a count of 128, pin 14 goes high.

With these descriptions of chips IC1, IC2 and IC3 in mind, the system operation will now be described.

Resistors 58 and 68 have impedances such that when diodes 62 and 66 are reverse biased, the escape interval of chip IC1 is 2.5 seconds. (As mentioned above, it is advisable for a practical pacer to have a programming capability so that the escape interval can be changed at the will of the physician; such a feature is not shown in the drawing for the sake of simplicity, inasmuch as it is not necessary for an understanding of the features of the invention.) As long as the heart is beating at intervals which do not exceed 2.5 seconds, each detected heartbeat results in a negative pulse at pins 15, 16. On the rising edge of the pulse at pin 3 of chip IC2, the upper flip-flop is clocked. Since a heartbeat has been detected, pins 3, 4 remain at a high potential and the D1 input at pin 5 is high. Consequently, the upper flip-flop is continuously clocked to the set state, and output Q1 remains high. Diode 62 is reverse biased and resistor 60 effectively remains out of the circuit. As will become apparent below, the lower flip-flop is initially in the set state, with its Q2 output high, so that resistor 64 is also effectively out of the circuit.

But if 2.5 seconds elapse without a spontaneous heartbeat having been detected, chip IC1 generates a stimulus and pins 3, 4 are now pulsed low at the same time that pins 15, 16 are pulsed low. Since the upper flip-flop is clocked on the trailing edge of the pulse at pins 15, 16, at which time pins 3, 4 are still low in potential, the upper flip-flop is reset and the Q1 output goes low. The negative pulse at pins 3, 4 also causes the count in counter chip IC3 to be incremented. Not only is the count of the number of 2.5-second pauses thus incremented but, because diode 62 is now forward biased, resistor 60 operates to lower the total impedance seen at pins 13, 14 of chip IC1. Consequently, the escape interval is reduced to 1.2 seconds; the fact that a pause has occurred is sufficient reason to change the mode of operation to a normal demand mode, with a normal escape interval of 1.2 seconds. With the upper flip-flop reset, its $\overline{Q1}$ output is high and this potential is extended through diode 72 to pin 2 of counter chip IC3. As chip IC1 continues to generate stimulating pulses, as they are required, the negative pulses at pins 3, 4 no longer appear at pin 2 of chip IC3 so that the count remains fixed.

For as long as the patient's heart does not beat spontaneously and chip IC1 times out at the end of successive 1.2-second intervals, pacing pulses are generated continuously and the count remains fixed. But the first time that the patient's heart beats spontaneously, before the end of a 1.2-second time-out, the negative pulse at pins 15, 16 is not accompanied by a negative pulse at pins 3, 4 of chip IC1. The trailing edge of the pulse at the CL1 input of chip IC2 causes the upper flip-flop to switch to the set state because the D1 input remains high. With the Q1 output now being switched high, diode 62 is reverse biased so that the escape interval reverts to 2.5 seconds; with the $\overline{Q1}$ output now being low, the next negative pulse at pins 3, 4 of chip IC1, representing a 2.5-second pause, can control the incrementing of the count in chip IC3.

When the count cycles from 127 to 128, pin 14 goes high in potential. Because pin 14 is connected to the R1 and S2 inputs of chip IC2, the upper flip-flop is held reset and the lower flip-flop is held set. The upper flip-flop was reset by the same pulse at pins 3, 4 of chip IC1 that incremented the count in chip IC3 and it is now held reset permanently; even if a spontaneous beat is detected within the 1.2-second escape interval, the upper flip-flop cannot be set, the $\overline{Q1}$ output remains high, and the counter is inhibited from counting. The pacer continues to operate in the demand mode, with an escape interval of 1.2 seconds. The lower flip-flop was initially set with its Q2 output being high so that resistor 64 cannot shorten the escape interval, and with its $\overline{Q2}$ output being low so that it has no effect on the upper flip-flop. With a high potential now applied to the S2 input, the lower flip-flop remains in this set state.

There is no reason to count about 128 pauses; if this many pauses have occurred, upon interrogation the physician will determine that the patient suffers from a bradycardia condition, and the exact number of pulses above 128 is not really that important. (If it is, a counter with a great number of bit positions may be employed.)

Reed switch 40, across which a conventional debouncing capacitor 38 is placed, is normally open. Consequently, a positive potential appears at the cathode of diode 34 so that chip IC1 can be re-triggered by detected heartbeats, and the base of transistor T1 is held high so that the device remains off. Capacitor 78 is charged, and the junction of the capacitor and resistor 80 is at ground potential so that neither of reset pins 7 and 15 of chip IC3 is energized. When an external magnet is brought into the vicinity of the reed switch, the switch closes and a ground potential appears at the cathode of diode 34. The low potential at pins 17, 18 disables chip IC1 from being re-triggered by pulses at the output of comparator 20, and the chip operates in a free-running mode to generate pacing pulses continuously at pins 9, 10. Together with each pacing pulse, negative pulses appear at pins 3, 4 and 15, 16.

The same reed switch closure discharges capacitor 78, but the negative pulse extended through the capacitor to pins 7, 15 of chip IC3 has no effect on the chip. The low potential extended through resistor 76 to the base of transistor T1, however, does turn this transistor on, and the current flowing through collector resistor 74 results in a positive step being applied to clock input CL2 of chip IC2.

Assuming that the counter did not reach the maximum count of 128, pin 14 of chip IC3 is still low in potential so that the upper flip-flop is not held reset and the lower flip-flop is not held set. The rising edge at the CL2 input of the lower flip-flop causes the device to reset since the D2 input is grounded. The Q2 output at pin 13 goes low to forward bias diode 66. The $\overline{Q2}$ output at pin 12 goes high and since it is connected to the S1 input of the upper flip-flop, the upper flip-flop is held in the set state; its Q1 output is high so that diode 62 is reverse biased, and the $\overline{Q1}$ output is low so that chip IC3 can count the pulses generated at pins 3, 4 of chip IC1. With resistor 64 effectively connected in parallel with resistor 68 and resistor 60 effectively out of the circuit, chip IC1 functions with the lowest escape interval, a value which controls the generation of pulses at a rate of 80 per minute. Since the chip now generates pulses continuously, the relatively rapid (but not dangerously fast) pulses appear on an EKG trace. Eventually, a count of 128 is reached in chip IC3, and pin 14 goes high. At this time, the upper flip-flop is reset and the lower flip-flop is set. In this state, the 1.2-second escape interval applies, and because the $\overline{Q1}$ output is high no further pulses are counted. The pacer simply continues to operate in a continuous mode, with a 1.2-second escape interval.

The physician can determine the number of pauses which have occurred since the last interrogation simply by counting the number of pulses which are generated at the 80 beat-per-minute rate and subtracting this number from 128. If the maximum number of pauses was counted prior to interrogation, pin 14 of chip IC3 will be high prior to application of the external magnet, and no pulses will be generated at the fast rate. Consequently, the physician will be able to determine that 128 pauses occurred.

Upon release of the magnet and the opening of switch 40 after the reporting interval, chip IC1 is once again allowed to operate in the demand mode. Transistor T1 now turns off, the negative edge at the CL2 input of chip IC2 having no effect on the lower flip-flop. The positive step extended through capacitor 78 to reset pins 7 and 15 of chip IC3 causes the counter to reset from a count of 128 to a count of zero so that a new counting sequence can begin. The positive potential which is extended through diode 82 to the R1 and S2 inputs of chip IC2, until capacitor 78 has fully charged, holds the upper flip-flop reset and the lower flip-flop set. With the lower flip-flop in the set state, resistor 64 is effectively out of the circuit. With the upper flip-flop in the reset state, resistor 60 is in the circuit, and the escape interval is 1.2 seconds.

The flip-flops are held in these states until capacitor 78 charges and the positive potential is removed from inputs R1 and S2 of chip IC2. The first heatbeat which occurs at sinus rhythm (within 1.2 seconds of the preceding beat) results in the setting of the upper flip-flop so that the 2.5-second escape interval applies once again.

It should be noted that the first pulse at pins 3, 4 of chip IC1 which occurs following application of the magnet may result in incrementing the counter before the Q2 output of chip IC2 goes low to control an 80 pulse-per-minute rate, depending on the system switching speeds; in such a case, the physician should be informed that the number of pauses which occurred may actually be one less than that described above.

Thus far it has been assumed that the magnet is held in place over the chest of the patient during the entire interrogation by the physician. If the magnet is applied only momentarily and is removed before counter IC3 has counted to 128, a different result ensues. In fact, if the patient feels discomfort due to the long, 2.5-second, escape interval he should do precisely this.

The short positive pulse at the base of transistor T1 is sufficient to clock the lower flip-flop so that the lower flip-flop is reset and the upper flip-flop is set, thus giving rise to a continuous 80 pulse-per-minute rate and to continued incrementing of counter chip IC3. As soon as the magnet is removed, a positive step would ordinarily be applied through capacitor 78. However, pin 14 is low in potential and diode 82 prevents reset pins 7 and 15 from being pulsed high. Chip IC3 continues to count to 128 and only when the maximum count is reached does pin 14 go high. The upper flip-flop is reset, the lower flip-flop is set, and the escape interval is changed to 1.2 seconds.

While the count is incrementing after the reed switch opens, pins 17, 18 of chip IC1 can sense heartbeats. As a practical matter, however, no natural heatbeats are sensed since the escape interval is so short, corresponding to 80 beats per minute. Once a count of 128 is reached, the pacer continues to operate in the demand mode, with an escape interval of 1.2 seconds. In this way the patient can control normal operation of the pacer, after rapid cycling of chip IC3 to a count of 128, simply by placing the magnet over his chest momentarily. (The pacer can be controlled to operate with hysteresis once again by applying the magnet one more time, in order to reset counter chip IC3. If the physician is unaware of the current state of the pacer, he should hold the magnet in place until continuous pulses are generated 1.2 seconds apart. Removal of the magnet will then cause the pacer to operate with hysteresis; another application of the magnet, this time only momentarily, will switch the mode to normal demand operation after 128 fast pulses are generated).

A patient who suffers from sick-sinus syndrome exhibits periods of slow heartbeats. While he may report to his physician that he has dizzy spells, the physician has no way of telling whether the dizziness is being caused by periods of slow heartbeats or something else. One of the main advantages of the pacer of FIG. 1 is that it allows the physician to count the number of pauses during any period of interest so that sick-sinus syndrome can be confirmed. An important advantage of the external magnet control is that it even allows some diagnostic tests to be performed without physician intervention. For example, the physician may want the patient to take a particular drug in order to test its effect, but the drug should perhaps be taken in the evening when the patient is not in the physician's office. In such a case, the patient may be told to take the drug and to then hold the magnet over his chest in order to reset the counter. In this way, the count of the number of pauses which occur can commence with the taking of the drug, or some predetermined time thereafter.

It is to be understood that although the "hysteresis" type of operation with the pacer of FIG. 1 involves escape intervals of 2.5 and 1.5 seconds, in actual practice it would be preferred to allow the two escape intervals to be programmed by the physician, just as other parameters may be programmed. Present-day programming systems are so advanced that illustration is not necessary.

The system of FIG. 1 simply counts the number of 2.5-second pauses. As described above, howeve, in some cases a number of slightly slower heartbeats in succession may be considered together to be a single "pause" event of interest. The add-on circuit of FIG. 2 treats each sequence of four successive pulses whose inter-pulse intervals are greater than 2 seconds but less than 2.5 seconds as being a single event of interest which results in the incrementing of the total "pause" count.

Pins 15, 16 of chip IC1, in addition to being connected as shown in FIG. 1, are also connected to an input of inverter 84. Each beat thus results in a short positive pulse appearing at the output of the inverter. This pulse enables one input of each of gates 90 and 92, and it also triggers 2-second monostable multivibrator 88 after being delayed by about 1 millisecond by delay element 86. The 2-second negative pulse at the output of the multivibrator is applied to the second input of gate 90, and to the second, inverting, input of gate 92 as well.

As long as heartbeats are detected at less than 2-second intervals, the positive pulse applied by inverter 84 to one input of gate 90 always arrives while the Q output of multivibrator 88 is still low so that the output of gate 90 remains low.

If pulses appear at pins 15, 16 of chip IC1 separated by more than 2 seconds, the multivibrator output has gone high by the time each pulse arrives. In such a case, both inputs of gate 90 are energized, the output goes high, and divide-by-four counter 94 is clocked. The purpose of delay element 86 is to allow gate 90 to operate before the multivibrator is triggered; without the delay, gate 90 might not have sufficient time to operate before its input connected to the multivibrator goes low as a result of the multivibrator triggering by the same positive pulse at the output of inverter 84 which passes through the gate.

Counter 96 counts four pulses, and its output goes high after the fourth pulse is counted. The output of the counter is connected to one input of OR gate 98. Instead of the junction of resistor 70 and diode 72 being connected directly to pin 2 of chip IC3 as shown in FIG. 1, this junction is connected to the other input of the OR gate, and it is the output of the OR gate which is connected to pin 2 of chip IC3. In this way, the count is incremented not only for each 2.5 second pause, but also whenever counter 96 reaches a count of 4.

The circuit of FIG. 2, however, should increment the count in chip IC3 only if four heartbeats in succession occur with an inter-beat interval which is greater than 2 seconds. Should any heartbeat be detected before 2 seconds have expired following the preceding beat, the output of multivibrator 88 will be low so that the inverting input of gate 92 will be high. The pulse at the output of inverter 84 is applied directly to the other input of gate 92, so that the output of the gate goes high. The resulting pulse is extended through OR gate 94 to the reset input of counter 96 so that the count in progress is aborted. Also, if a pause of 2.5 seconds occurs, the count in chip IC3 will be incremented anyway, and the count in counter 96 should be reset. As shown in FIG. 2, pins 3, 4 of chip IC1 are connected to an inverting input of OR gate 94. Thus each negative pulse from chip IC1 which represents the generation of a stimulus resets counter 96. (Although pulses at pins 3, 4 of chip IC1 also occur when the pacer is operating in the normal demand mode with a 1.2-second escape interval, there is no reason not to reset counter 96 upon the occurrence of each such pulse inasmuch as it does not follow a 2-second inter-pulse interval.)

It should be noted that the add-on circuit of FIG. 2 does not change the basic system operation at all, other than to allow counter chip IC3 to be incremented following four successive short pauses. (It will be apparent, of course, that the maximum count of counter 96 could be programmable, as could the period of multivibrator 88.) As mentioned above, if it is important to distinguish between the two kinds of pauses, two separate counters could be provided, the circuit of FIG. 2 serving to increment an additional counter which would operate in a manner similar to the operation of chip IC3. In such a case, the two counters should count up to 128 in succession following interrogation, a delay being introduced between the two pulsings at an 80 pulse-per-minute rate, such a control mechanism being apparent to those skilled in the art.

Although the invention has been described with reference to a particular embodiment, it is to be understood that this embodiment is merely illustrative of the application of the principles of the invention. Numerous modifications may be made therein and other arrangements may be devised without departing from the spirit and scope of the invention.

We claim:

1. An implantable heart pacer comprising means for generating pacing pulses, means for sensing heart activity, means for controlling said generating means to generate pacing pulses at times dependent upon when heart activity was sensed, means responsive to said sensing means for counting heartbeat pauses which exceed a first predetermined interval and sequential heartbeat pauses of a predetermined number each of which exceeds a second shorter predetermined interval, and means for reporting on the state of said counting means.

2. An implantable heart pacer in accordance with claim 1 wherein said counting means is reset upon operation of said reporting means.

3. An implantable heart pacer in accordance with claim 2 wherein said reporting means controls the generation of a sequence of pacing pulses whose number is dependent upon the state of said counting means.

4. An implantable heart pacer in accordance with claim 3 wherein the pacing pulses generated under control of said reporting means are generated at a continuous rate which is faster than any rate controlled by said controlling means.

5. An implantable heart pacer in accordance with claim 4 wherein said reporting means operates responsive to the application of an external magnet in the vicinity thereof.

6. An implantable heart pacer in accordance with claim 5 wherein a pause which exceeds said first predetermined interval is indicative of a bradycardia condition.

7. An implantable heart pacer in accordance with claim 6 wherein said controlling means causes the pacer to operate in a demand mode with a first escape interval equal to said first predetermined interval following the sensing of heart activity within a second shorter escape interval equal to said second predetermined interval, and causes the pacer to operate in a demand mode with said second escape interval following the sensing of heart activity within said first escape interval.

8. An implantable heart pacer in accordance with claim 7 further including means responsive to the state of said counting means reaching a predetermined state for thereafter causing the pacer to operate in a demand mode with said second escape interval, without changing to said first escape interval dependent upon the sensing of heart activity.

9. An implantable heart pacer in accordance with claim 8 further including means operative responsive to the reporting on the state of said counting means, even said predetermined state, for allowing the pacer to once again operate in a demand mode with said first escape interval.

10. An implantable heart pacer in accordance with claim 9 wherein the mode in which the pacer operates varies with the manner in which said external magnet is applied in the vicinity of the pacer, the pacer being operable in one mode in which the escape interval changes between shorter and longer values in accordance with sensed heart activity and in another mode in which the escape interval is always the shorter of the two and is independent of sensed heart activity.

11. An implantable heart pacer in accordance with claim 1 wherein said reporting means controls the generation of a sequence of pacing pulses whose number is dependent upon the state of said counting means.

12. An implantable heart pacer in accordance with claim 11 wherein the pacing pulses generated under control of said reporting means are generated at a continuous rate which is faster than any rate controlled by said controlling means.

13. An implantable heart pacer in accordance with claim 12 wherein said reporting means operates responsive to the application of an external magnet in the vicinity thereof.

14. An implantable heart pacer in accordance with claim 13 wherein a pause which exceeds said first predetermined interval is indicative of a bradycardia condition.

15. An implantable heart pacer in accordance with claim 14 wherein the pacer operates in two different demand modes dependent upon the manner in which said external magnet is applied in the vicinity of the pacer, the pacer being operable in one mode in which the escape interval changes between shorter and longer values in accordance with sensed heart activity and in another mode in which the escape interval is always the shorter of the two and is independent of sensed heart activity.

16. An implantable heart pacer in accordance with claim 1 wherein said reporting means operates responsive to the application of an external magnet in the vicinity thereof.

17. An implantable heart pacer in accordance with claim 16 wherein the pacer operates in two different demand modes dependent upon the manner in which said external magnet is applied in the vicinity of the pacer, the pacer being operable in one mode in which the escape interval changes between shorter and longer values in accordance with sensed heart activity and in another mode in which the escape interval is always the shorter of the two and is independent of sensed heart activity.

18. An implantable heart pacer in accordance with claim 1 wherein a pause which exceeds said first predetermined interval is indicative of a bradycardia condition.

19. An implantable heart pacer in accordance with claim 18 wherein said controlling means causes the pacer to operate in a demand mode with a first escape interval equal to said first predetermined interval following the sensing of heart activity within a second shorter escape interval equal to said second predetermined interval, and causes the pacer to operate in a demand mode with said second escape interval following the sensing of heart activity within said first escape interval.

20. An implantable heart pacer in accordance with claim 19 further including means responsive to the state of said counting means reaching a predetermined state for thereafter causing the pacer to operate in a demand mode with said second escape interval, without changing to said first escape interval dependent upon the sensing of heart activity.

21. An implantable heart pacer in accordance with claim 20 further including means operative responsive to the reporting on the state of said counting means, even said predetermined state, for allowing the pacer to once again operate in a demand mode with said first escape interval.

22. An implantable heart pacer in accordance with claim 21 wherein the mode in which the pacer operates varies with the manner in which said external magnet is applied in the vicinity of the pacer, the pacer being operable in one mode in which the escape interval changes between shorter and longer values in accordance with sensed heart activity and in another mode in which the escape interval is always the shorter of the two and is independent of sensed heart activity.

23. An implantable heart pacer in accordance with claim 1 wherein said controlling means causes the pacer to operate in a demand mode with a first escape interval following the sensing of heart activity within a second shorter escape interval, and causes the pacer to operate in a demand mode with said second escape interval following the sensing of heart activity within said first escape interval.

24. An implantable heart pacer in accordance with claim 23 further including means responsive to the state of said counting means reaching a predetermined state for thereafter causing the pacer to operate in a demand mode with said second escape interval, without changing to said first escape interval dependent upon the sensing of heart activity.

25. An implantable heart pacer in accordance with claim 24 further including means operative responsive to the reporting on the state of said counting means, even said predetermined state, for allowing the pacer to once again operate in a demand mode with said first escape interval.

26. An implantable heart pacer in accordance with claim 25 wherein the mode in which the pacer operates varies with the manner in which said external magnet is applied in the vicinity of the pacer, the pacer being operable in one mode in which the escape interval changes between shorter and longer values in accordance with sensed heart activity and in another mode in which the escape interval is always the shorter of the two and is independent of sensed heart activity.

27. An implantable heart pacer in accordance with claim 1 wherein the pacer operates in two different demand modes dependent upon the manner in which an external magnet is applied in the vicinity of the paer, the pacer being operable in one mode in which the escape interval changes between shorter and longer values in accordance with sensed heart activity and in another mode in which the escape interval is always the shorter of the two and is independent of sensed heart activity.

* * * * *